US011439723B1

(12) United States Patent
Battersby

(10) Patent No.: US 11,439,723 B1
(45) Date of Patent: Sep. 13, 2022

(54) DISINFECTANT MISTING SYSTEM AND ASSEMBLY

(71) Applicant: AIR PROFECTO LLC, Fort Lauderdale, FL (US)

(72) Inventor: Nicholas Battersby, Fort Lauderdale, FL (US)

(73) Assignee: AIRSEBY CORPORATION, Wilton Manors, FL (US)

( * ) Notice: Subject to any disclaimer, the term of this patent is extended or adjusted under 35 U.S.C. 154(b) by 0 days.

(21) Appl. No.: 17/606,970

(22) PCT Filed: Jun. 29, 2021

(86) PCT No.: PCT/US2021/039643
§ 371 (c)(1),
(2) Date: Oct. 27, 2021

(87) PCT Pub. No.: WO2022/006127
PCT Pub. Date: Jan. 6, 2022

Related U.S. Application Data

(60) Provisional application No. 63/045,797, filed on Jun. 29, 2020.

(51) Int. Cl.
*A61L 9/14* (2006.01)
(52) U.S. Cl.
CPC .............. *A61L 9/14* (2013.01); *A61L 2209/11* (2013.01); *A61L 2209/134* (2013.01)
(58) Field of Classification Search
CPC . A61L 2/18; A61L 2/183; A61L 2/186; A61L 2/22; A61L 2/24; A61L 9/14; A61L 2202/11; A61L 2202/15; A61L 2202/25; A61L 2209/11; A61L 2209/134
See application file for complete search history.

(56) References Cited

U.S. PATENT DOCUMENTS

| 3,096,775 | A | 7/1963 | Clarke et al. |
| 5,993,739 | A | 11/1999 | Lyon |
| 6,427,707 | B1 | 8/2002 | Morris |
| 7,306,167 | B2 | 12/2007 | Colarusso et al. |
| 11,135,330 | B1 * | 10/2021 | Craig ............... A62C 35/68 |
| 2010/0146587 | A1 | 10/2010 | Sholes et al. |
| 2010/0290958 | A1 | 11/2010 | Brents et al. |
| 2011/0315175 | A1 | 12/2011 | Lella et al. |
| 2012/0107184 | A1 | 5/2012 | Asiyanbola et al. |
| 2015/0190538 | A1 | 7/2015 | Olvera et al. |

* cited by examiner

*Primary Examiner* — Timothy C Cleveland
(74) *Attorney, Agent, or Firm* — Mark C. Johnson; Johnson Dalal

(57) ABSTRACT

A disinfectant misting system and assembly operably configured to selectively control emission of an atomized spray of disinfectant solution within an enclosed structure at desired times, in desired locations, and for a desired amount of flow through at least one electronic control unit in an effective and efficient manner, and comprising a liquid supply housing with a liquid disinfectant storage tank housing a disinfectant solution, a disinfectant supply pump, an electronically controlled room pressure regulation component, and an electronically controlled pump pressure regulation component fluidly couplable to a liquid conduit assembly operably configured to transport the disinfectant solution to at least one disinfectant emission housing operably configured to emit an atomized spray of the disinfectant solution into the enclosed room space.

17 Claims, 12 Drawing Sheets

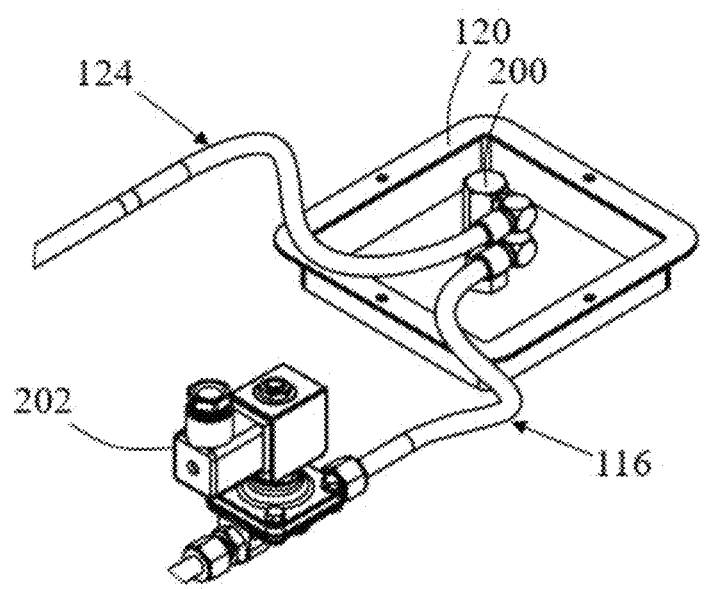
A
FIG. 2
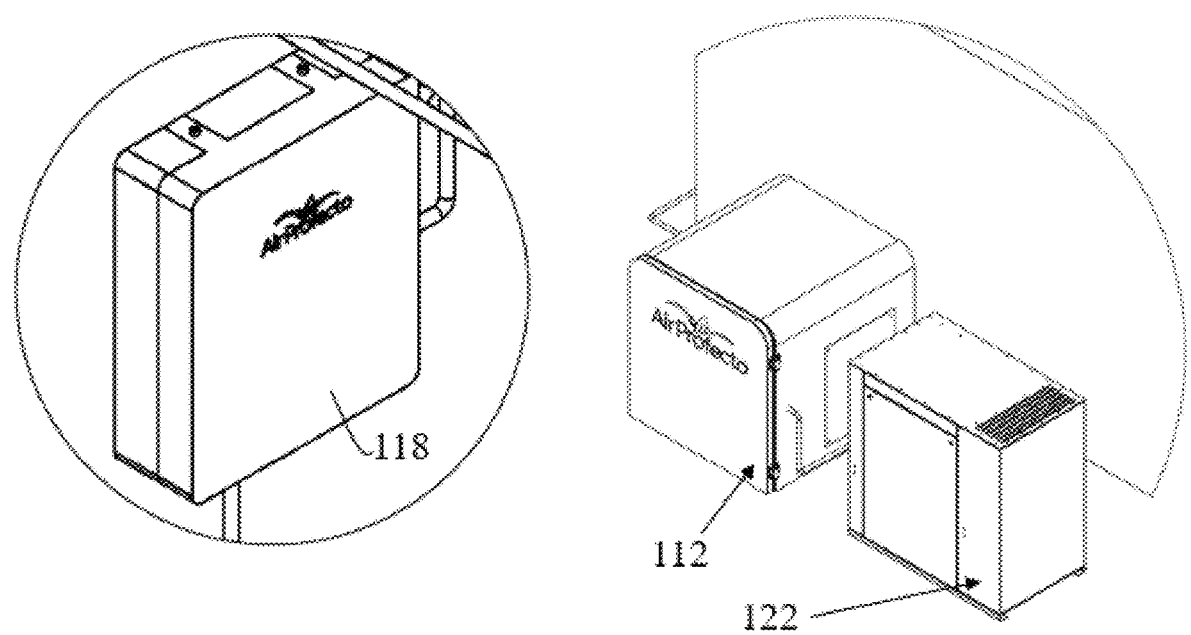
B
FIG. 3
C
FIG. 4

DISINFECTANT MISTING SYSTEM AND ASSEMBLY

FIELD OF THE INVENTION

The present invention relates generally to sanitizers and disinfectants, and, more particularly, relates to a disinfectant misting system and assembly operably configured to emit an atomized spray of a disinfectant solution within an enclosed structure.

BACKGROUND OF THE INVENTION

The effective and continuous sanitation or disinfection of common and public areas has significantly grown in importance over time. Specifically, the ability to kill germs, bacteria, viruses, and other pathogens or microorganisms in enclosed structures or spaces has become more valuable and many businesses, retail locations, and commercial and residential buildings have exhibited a demand for systems and assemblies with the foregoing capabilities. Although there are a number of assemblies known in the industry that are designed to achieve the goal of sanitizing and disinfecting large spaces and enclosed structures, said existing prior art is characterized by several significant limitations. See, e.g., Lella et al., U.S. Patent Application Publication No. 2011/0315175 A1 (Dec. 29, 2011); Brents et al., U.S. Patent Application Publication No. 2010/0290958 A1 (Nov. 18, 2010); Olvera et al., U.S. Patent Application Publication No. 2015/0190538 A1 (Jul. 9, 2015). For one, the existing configurations do not comprise an efficient and effective pressure and flow distribution network. Specifically, it is difficult for the known systems to manage pressure drops over longer distances within their conduit assemblies, resulting in a significant loss or decrease in the pressure and flow of the disinfectant solution when it is eventually emitted. To that end, the electronically controlled valves in the existing prior art are not arranged in a position or configuration that facilitates the effective distribution and emission of the disinfectant solution into the enclosed space. This limitation prevents the disinfectant solution from being distributed over a large surface area within the enclosed space. Further, the disinfectant solution used in existing configurations does not specifically disclose a hypochlorous acid constituent.

Therefore, a need exists to overcome the problems with the prior art as discussed above.

SUMMARY OF THE INVENTION

The invention provides a disinfectant misting system and assembly that overcomes the hereinafore-mentioned disadvantages of the heretofore-known devices and methods of this general type and that effectively and efficiently sanitizes, disinfects, distributes, and emits a disinfectant solution into any number of predetermined enclosed spaces. The intermediate valves disbursed throughout the liquid conduit assembly facilitate an efficient and effective pressure and flow distribution network that reduces the loss of pressure, flow, and energy at disinfectant emission housings. This beneficial feature prevents significant pressure drops over longer distances within the liquid conduit assembly such that the disinfectant solution is emitted with sufficient pressure to evenly distribute the solution over a greater area and volume of the enclosed space. The present invention also contains a hypochlorous acid constituent which aids in disinfecting and sanitizing the enclosed space over which the disinfectant solution is distributed.

With the foregoing and other objects in view, there is provided, in accordance with the invention, a disinfectant misting system implemented within an enclosed structure having a structure sidewall, a ground wall, and a ceiling wall defining an enclosed room space and comprising a liquid supply housing with a liquid disinfectant storage tank housing a disinfectant solution and fluidly couplable, through a liquid conduit assembly, with a disinfectant generation unit fluidly couplable, through the liquid conduit assembly, to a liquid supply source, the liquid disinfectant storage tank and the disinfectant generation unit selectively fluidly couplable to one another through an electronically controlled tank valve; a disinfectant supply pump housed within the liquid supply housing and operably configured to receive the disinfectant solution and induce, within the liquid conduit assembly, a selectively controlled flow rate thereon downstream of the liquid disinfectant storage tank and to an electronically controlled room pressure regulation component fluidly coupled to the liquid conduit assembly and housed within at least one intermediate regulation housing coupled to the structure sidewall; an electronically controlled pump pressure regulation component housed within the liquid supply housing and fluidly coupled to the liquid conduit assembly downstream of the disinfectant supply pump and upstream of the electronically controlled room pressure regulation component; at least one disinfectant emission housing coupled to the ceiling and including an emission lower wall, an emission housing sidewall surrounding and coupled to the emission lower wall, and at least one emission nozzle retained thereon, fluidly coupled to the liquid conduit assembly, and operably configured to emit an atomized spray of the disinfectant solution through an emission port defined thereon, in a direction away from the at least one disinfectant emission housing, and into the enclosed room space; and at least one electronic control unit communicatively coupled to the electronically controlled tank valve, the disinfectant supply pump, the electronically controlled room pressure regulation component, and the electronically controlled pump pressure regulation component and operably configured to selectively regulate pressure within the liquid conduit assembly and selectively induce the controlled flow rate through the disinfectant supply pump and cause emission of the atomized spray of the disinfectant solution through the emission port on the at least one disinfectant emission housing and into the enclosed room space and at selectively controlled time intervals through use of a programmable timer.

In accordance with another feature, an embodiment of the present invention includes a compressed air assembly having a compressor operably configured to compress a gas downstream of the compressor within a gas conduit assembly spanning from the compressor to the at least one emission nozzle on the least one disinfectant emission housing; and an electronically controlled room air pressure regulator housed within the at least one intermediate regulation housing, fluidly coupled to the gas conduit assembly upstream of the at least one emission nozzle and downstream of the compressor, and operably configured to selectively modulate, through the at least one electronic control unit communicatively coupled thereto, the gas pressure within the gas conduit assembly downstream to the at least one emission nozzle, thereby causing an increased velocity distribution of the atomized spray of the disinfectant solution through the emission port on the at least one disinfectant emission housing.

In accordance with a further feature of the present invention, an embodiment of the present invention includes a gas supply housing with the compressor housed therein, with a refrigerated air dryer unit fluidly coupled to the gas conduit assembly downstream of the compressor, and with at least one filtering unit fluidly coupled to the gas conduit assembly downstream of the compressor and the refrigerated air dryer unit.

In accordance with yet another feature, an exemplary embodiment of the present invention comprises a plurality of disinfectant emission housings each coupled to the ceiling in a distribution configuration operably configured to supply the atomized spray of the disinfectant solution to at least 90% of a room area of the enclosed room space.

In accordance with an alternate embodiment of the present invention, the disinfectant generation unit is operably configured to generate the disinfectant solution by subjecting a liquid substance from the liquid supply source to an electrolytic chemical reaction within the disinfectant generation unit.

In accordance with a further feature of the present invention, an exemplary embodiment comprises a filtering unit fluidly coupled to the liquid conduit assembly and disposed downstream of the liquid supply source and upstream of the disinfectant generation unit.

In accordance with another feature of an exemplary embodiment, the disinfectant solution is hypochlorous acid.

In accordance with a further feature of the present invention, the system further comprises an electronically controlled emission pressure regulation component housed within the at least one disinfectant emission housing, fluidly coupled to the liquid conduit assembly downstream of the electronically controlled room pressure regulation component, and communicatively coupled to the at least one electronic control unit.

In accordance with an alternate embodiment of the present invention, the liquid supply housing further comprises a distribution unit housed therein and with a plurality of liquid conduits forming part of the liquid conduit assembly and operably configured to retain disinfectant solution downstream of the disinfectant supply pump, the plurality of liquid conduits spanning to separate and respective electronically controlled room pressure regulation components fluidly coupled thereto and housed within respective intermediate regulation housings coupled to respective structure sidewalls in respective enclosed room spaces.

In accordance with yet another embodiment of the present invention, the at least one disinfectant emission housing further comprises an emission port defining on four opposing sides of the housing sidewall of the at least one disinfectant emission housing; and a fan and an ultrasonic humidifier housed therein and operably configured to emit the atomized spray of the disinfectant solution through the emission ports defined on the four opposing sides of the housing sidewall of the at least one disinfectant emission housing.

Although the invention is illustrated and described herein as embodied in a disinfectant misting system and assembly, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms “a” or “an,” as used herein, are defined as one or more than one. The term “plurality,” as used herein, is defined as two or more than two. The term “another,” as used herein, is defined as at least a second or more. The terms “including” and/or “having,” as used herein, are defined as comprising (i.e., open language). The term “coupled,” as used herein, is defined as connected, although not necessarily directly, and not necessarily mechanically. The term “providing” is defined herein in its broadest sense, e.g., bringing/coming into physical existence, making available, and/or supplying to someone or something, in whole or in multiple parts at once or over a period of time. Also, for purposes of description herein, the terms “upper”, “lower”, “left,” “rear,” “right,” “front,” “vertical,” “horizontal,” and derivatives thereof relate to the invention as oriented in the figures and is not to be construed as limiting any feature to be a particular orientation, as said orientation may be changed based on the user’s perspective of the device. Furthermore, there is no intention to be bound by any expressed or implied theory presented in the preceding technical field, background, brief summary or the following detailed description.

As used herein, the terms “about” or “approximately” apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term “longitudinal” should be understood to mean in a direction corresponding to an elongated direction of the enclosed structure of the disinfectant misting system 100. The terms “program,” “software application,” and the like as used herein, are defined as a sequence of instructions designed for execution on a computer system.

A “program,” “computer program,” or “software application” may include a subroutine, a function, a procedure, an object method, an object implementation, an executable application, an applet, a servlet, a source code, an object code, a shared library/dynamic load library and/or other sequence of instructions designed for execution on a computer system.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

FIG. 2 is a fragmentary, perspective top view of a disinfectant emission housing and liquid conduit assembly, in accordance with an exemplary embodiment of the present invention;

FIG. 3 is a fragmentary, perspective top view of an intermediate regulation housing, in accordance with an exemplary embodiment of the present invention;

FIG. 4 is a perspective top view of a liquid supply housing, in accordance with an exemplary embodiment of the present invention;

DETAILED DESCRIPTION OF INVENTION

The invention described herein provides a disinfectant misting system and assembly that overcomes known disadvantages of those known devices and methods of this general type and that is operably configured to selectively control emission of an atomized spray of disinfectant solution at desired times, in desired locations, and for a desired amount of flow in an effective and efficient manner. In contrast with existing prior art, the present invention facilitates an efficient and effective pressure and flow distribution network that beneficially prevents significant pressure drops over longer distances within the liquid conduit assembly such that the disinfectant solution is emitted with sufficient pressure to evenly distribute the solution over a greater area and volume of the enclosed space. The foregoing feature, in conjunction with additional features and characteristics discussed herein, improves the overall disinfecting and sanitizing performance of the assembly.

Figure 1:
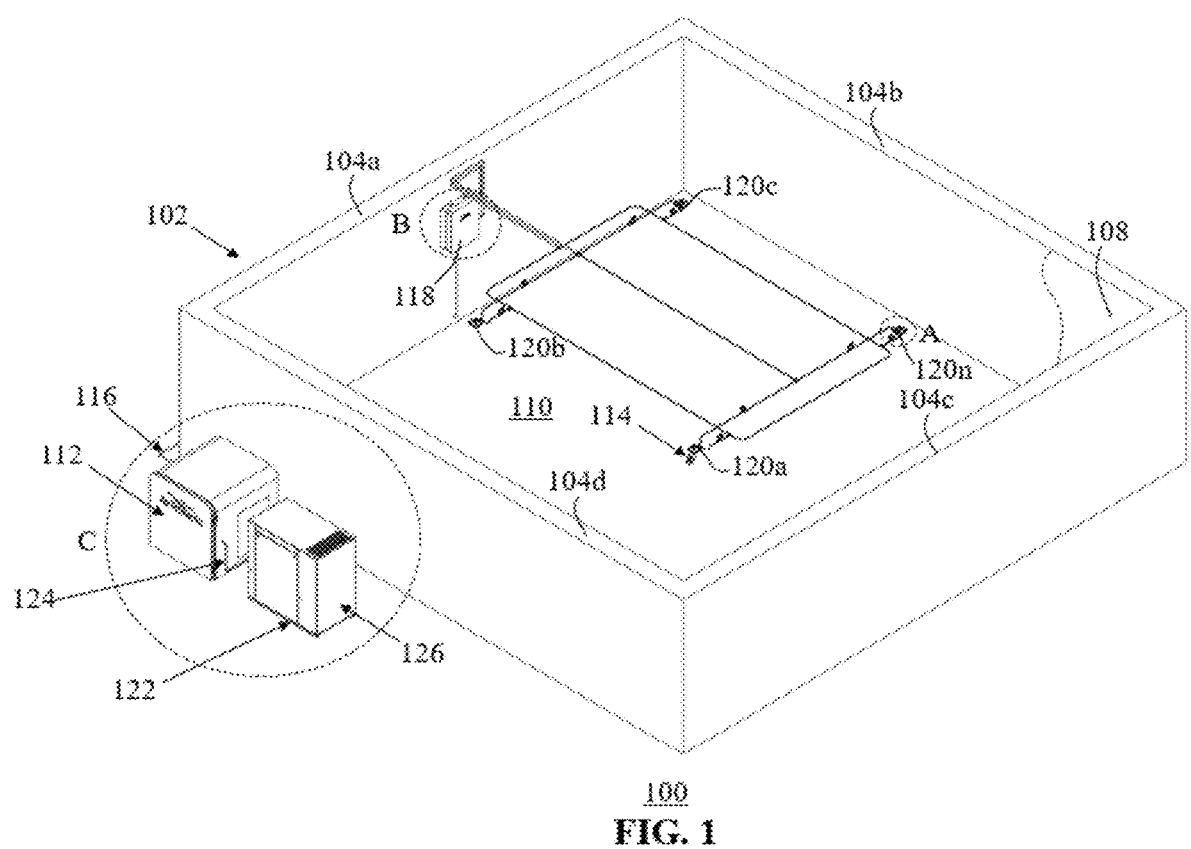
FIG. 1 is a perspective top view of a disinfectant misting system and assembly, in accordance with the present invention.

Referring now to FIG. 1, one embodiment of the present invention is shown in a perspective view. FIG. 1 depicted herein shows several advantageous features of the present invention, but, as will be described below, the invention can be provided in several shapes, sizes, combinations of features and components, and varying numbers and functions of the components. The first example of a disinfectant misting system and assembly 100 (hereinafter referred to as "system 100" for brevity), as shown in FIGS. 1-4, is implemented within an enclosed structure 102 having a structure sidewall 104, a ground wall 106, and a ceiling wall 108 defining an enclosed room space 110. The efficacy of the system 100 is optimal when the system 100 is utilized or applied in an enclosed and defined space which, as seen in FIG. 1, may be a room or building. As depicted in the fragmentary perspective views of FIGS. 12-15, however, various applications of the system 100 may be utilized in a variety of environments and on a variety of enclosed support structures 102, such as, by way of example and without limitation, a subway station and/or vehicle, an office building, a gymnasium, inside cabins and walkways of a cruise ship, inside the cabin of an airplane, and inside of a school building and bus, respectively. Depending on the configuration of the enclosed structure 102, the structure sidewall 104 may vary in shape, form, and number. In other words, the structure sidewall 104 should be construed to include circular structures having one continuous structure sidewall 104, as well as alternately configured structures having two or more structure sidewalls 104a-n, wherein "n" refers to any number greater than one, separately configured with respect to one another.

The system 100 comprises a liquid supply housing 112 (as best depicted in the exploded perspective view of FIG. 10) with a liquid disinfectant storage tank 1000 housing a disinfectant solution 114 and fluidly couplable, through a liquid conduit assembly 116, with a disinfectant generation unit 1002 fluidly couplable, through the liquid conduit assembly 116, to a liquid supply source 1100. The liquid disinfectant storage tank 1000 and the disinfectant generation unit 1002 may be selectively fluidly couplable to one another through an electronically controlled tank valve 1102. The liquid supply housing 112 may also include a cover panel 1012 and a door panel 1014 operably configured to encapsulate components of the liquid supply housing 112.

To accommodate enclosed structures 102 having a larger enclosed room space 110, or to avoid the need to repeatedly refill the liquid disinfectant storage tank 1000, the liquid disinfectant storage tank 1000 may have a volume of approximately 1 liter in exemplary embodiments of the present invention. The volume of the liquid disinfectant storage tank 1000 may vary, however, in accordance with the size of the enclosed room space 110 within which the system 100 is being utilized or applied, i.e., a smaller enclosed room space 110 may call for a smaller-sized liquid disinfectant storage tank 1000, whereas a larger enclosed room space 100 may require a liquid disinfectant storage tank 1000 having a larger volume and capacity.

Regardless of the specific size, the liquid disinfectant storage tank 1000 must be refilled periodically with the disinfectant solution 114, which may be done manually or automatically through remote means. To achieve improved sanitization and disinfection, the disinfectant solution 114 wholly consists of hypochlorous acid in one exemplary embodiment. Hypochlorous acid is a safe and effective broad spectrum antimicrobial agent because it is a non-cytotoxic, fully biocompatible chemical proven to be 100 times more effective at killing viruses than ordinary products containing bleach, but is a chemical that will not irritate the mucosa, cause skin irritation or trigger conditions like eczema with prolonged use. Hypochlorous acid is non-cytotoxic, biocompatible, and biodegradable. In view of the foregoing beneficial features and characteristics, hypochlorous acid is a preferred constituent of the disinfectant solution 114. In an exemplary embodiment, the pH level of the disinfectant solution 114 is between approximately 3.5 and 7.0, the cell life is approximately 4500 hours, and the available chlorine concentration is approximately 10-100 mg/L. In alternate embodiments, however, the disinfectant solution 114 may be of another comparable disinfecting and sanitizing chemical agent known in the industry to have beneficial disinfecting properties while remaining safe for use by humans.

The disinfectant generation unit 1002 is operably configured to receive liquid, e.g., municipal supply water in one embodiment, from the liquid supply source 1100 and to substantially disinfect the liquid from bacteria, mold, viruses, and other such impurities to create the disinfectant solution 114. In one embodiment, the disinfectant generation unit 1002 is operably configured to generate the disinfectant solution 114 by subjecting a liquid substance from the liquid supply source 1100 to an electrolytic chemical reaction within the disinfectant generation unit 1002. In a preferred embodiment, the disinfectant generation unit 1002 utilizes ultraviolet ("UV") light or rays to disinfect the liquid due to UV's strong germicidal or inactivating ability.

Figure 5:
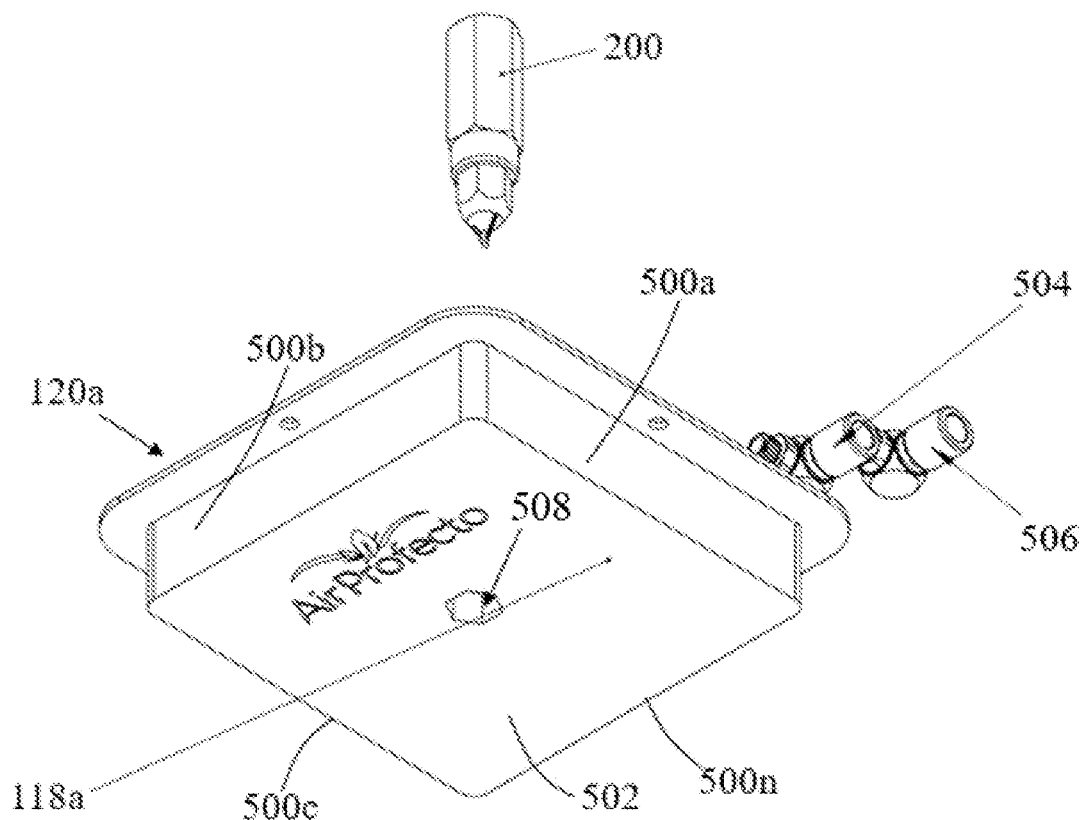
FIG. 5 is a perspective bottom view of one embodiment of a disinfectant emission housing, in accordance with the present invention.
Figure 6:
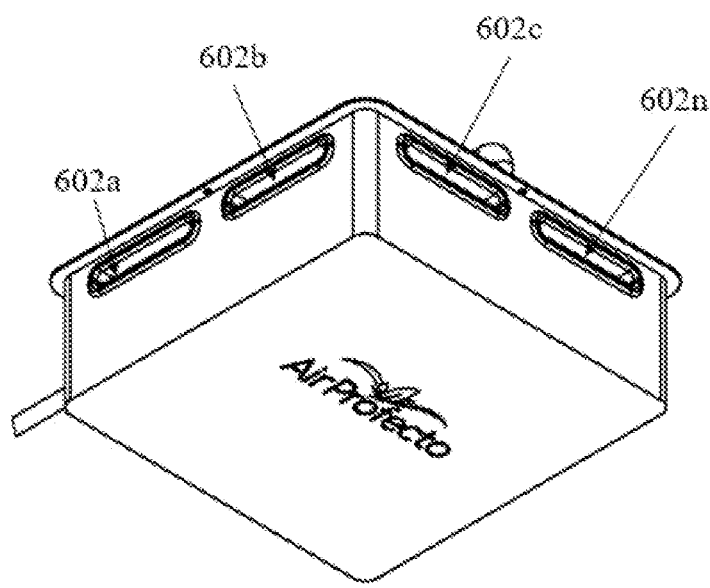
FIG. 6 is a perspective bottom view of a fan, in accordance with an exemplary embodiment of the present invention.
Figure 7:
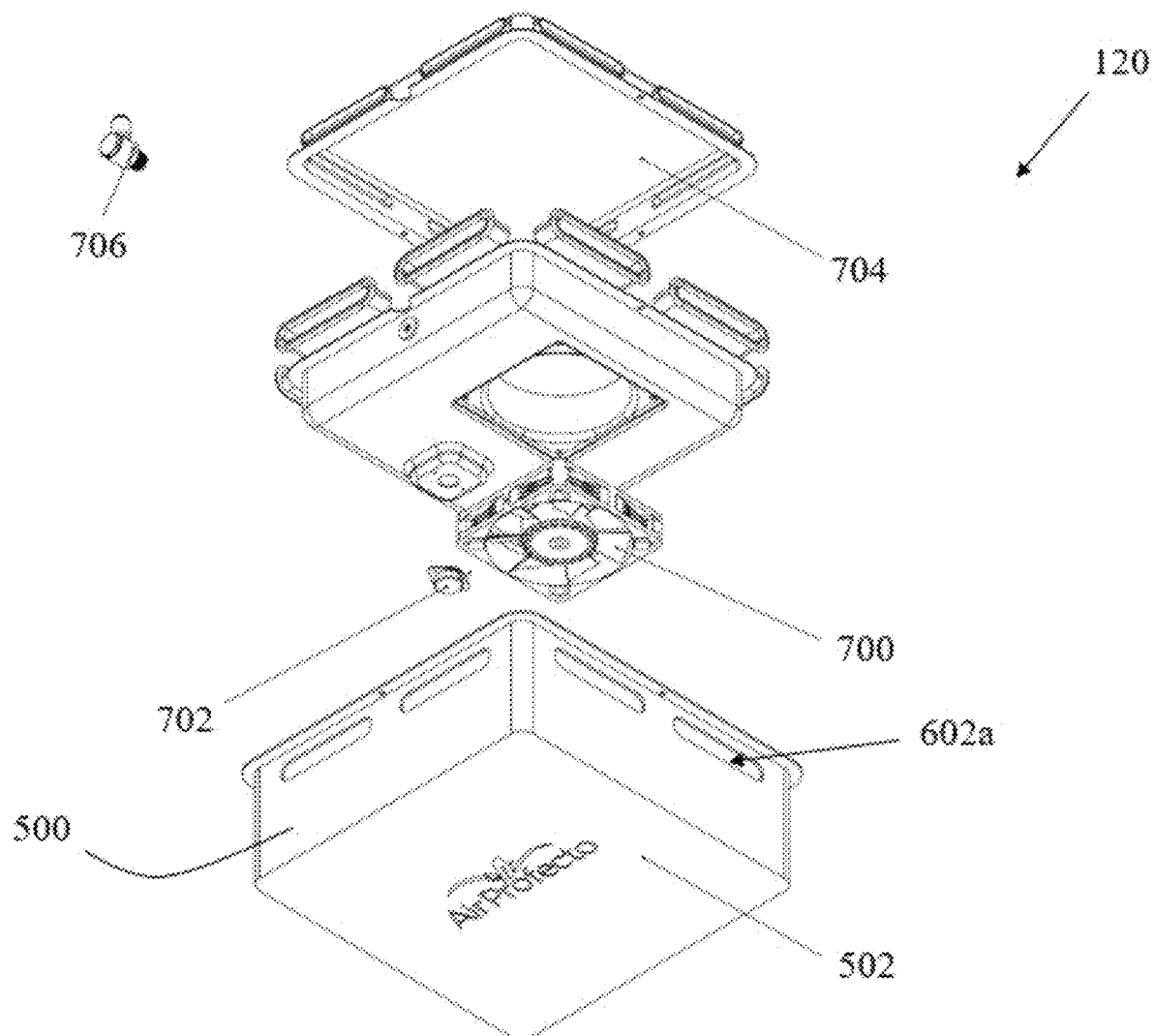
FIG. 7 is an exploded side view of a fan, in accordance with an exemplary embodiment of the present invention.

Specifically, UV disinfects water containing bacteria and viruses and can be effective against protozoans like, *Giardia lamblia* cysts or *Cryptosporidium* oocysts. UV has been commercially used for many years in the pharmaceutical, cosmetic, beverage, and electronics industries both within and outside the United States. In an exemplary embodiment, the disinfectant generation unit 1002 comprises a single UV bulb having a rated bulb life of approximately 12,000 hours, and is of a 304 stainless steel composition characterized by high corrosion resistance. The disinfectant generation unit 1002 further comprises threaded pipes fluidly couplable to the liquid conduit assembly 116 which, in one embodiment, have a maximum flow rate of 10 gpm, maximum pressure of 125 psi, and maximum temperature of 120° Fahrenheit. The liquid conduit assembly 116 may also consist of a plurality of pipes fluidly and/or threadedly coupled together to transport a liquid substance. In additional embodiments, as exemplified in FIG. 5, the intermediate regulation housings or other housings within the system may include one or more inlets 504, 506 for receiving a liquid or gas substance. As such, the inlets 504, 506 enable fluid coupling to the liquid conduit assembly 116 and/or gas conduit assembly 124.

In accordance with a further feature of a preferred embodiment of the present invention, the system 100 further comprises a filtering unit 1008 fluidly coupled to the liquid conduit assembly 116 and disposed downstream of the liquid supply source 1100 and upstream of the disinfectant generation unit 1002. The filtering unit 1008 is operably configured to filter out rust, sediment, and other comparable physical impurities and particles as small as 20 microns in size, from the liquid received by the disinfectant generation unit 1002 from the liquid supply source 1100. The filtering unit 1008 is fluidly coupled to the liquid conduit assembly 116 with threaded pipes having the following exemplary dimensions: 0.75-inch pipe size; maximum flow rate of 10 grams per minute; and maximum pressure of 125 psi. In some embodiments, the filtering unit 1008 may include one or more canisters fluidly coupled in a series to one another, each canister comprising water filtration components to filter out impurities from the liquid contained within the disinfectant solution 114. The filtering unit 1008 is disposed downstream of the liquid supply source 1100 and upstream of the disinfectant generation unit 1002 in order for the filtering unit 1008 to filter out physical impurities from the liquid first and then fluidly transport the filtered liquid to the disinfectant generation unit 1002, where the liquid is disinfected and sanitized to create the disinfectant solution 114 that is ultimately emitted.

Figure 11:
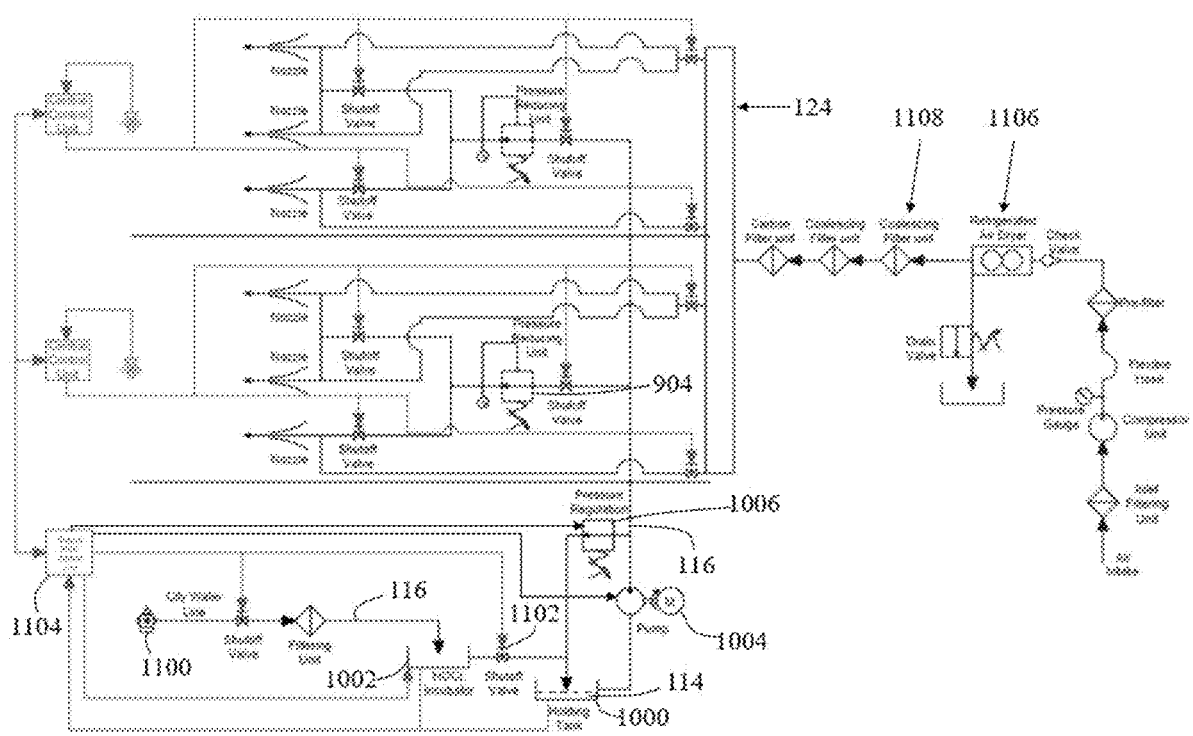
FIG. 11 is a schematic diagram of an exemplary disinfectant misting system and assembly, in accordance with the present invention.
Figure 12:
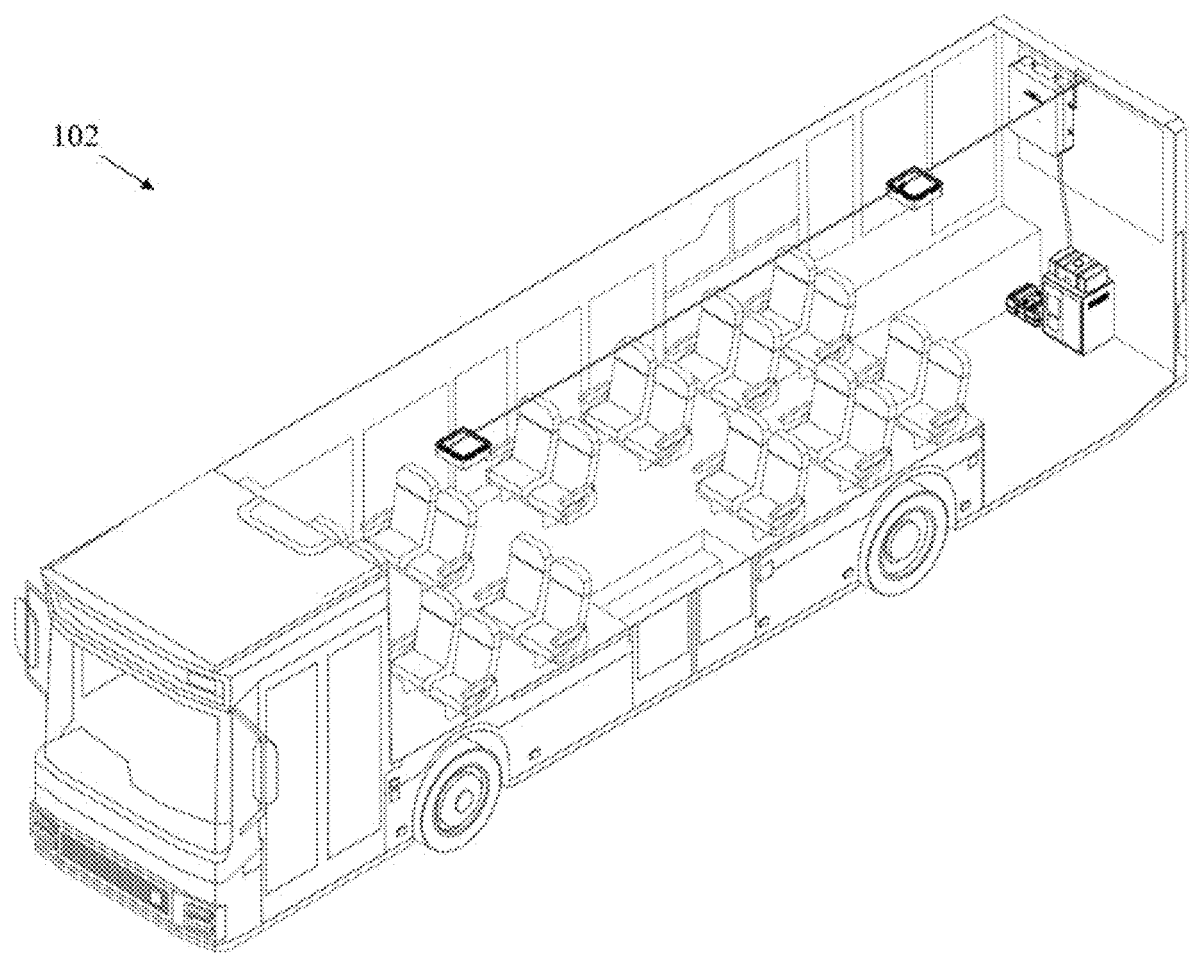
FIG. 12 is a fragmentary, perspective view of an enclosed bus structure, in accordance with one embodiment of the present invention.
Figure 13:
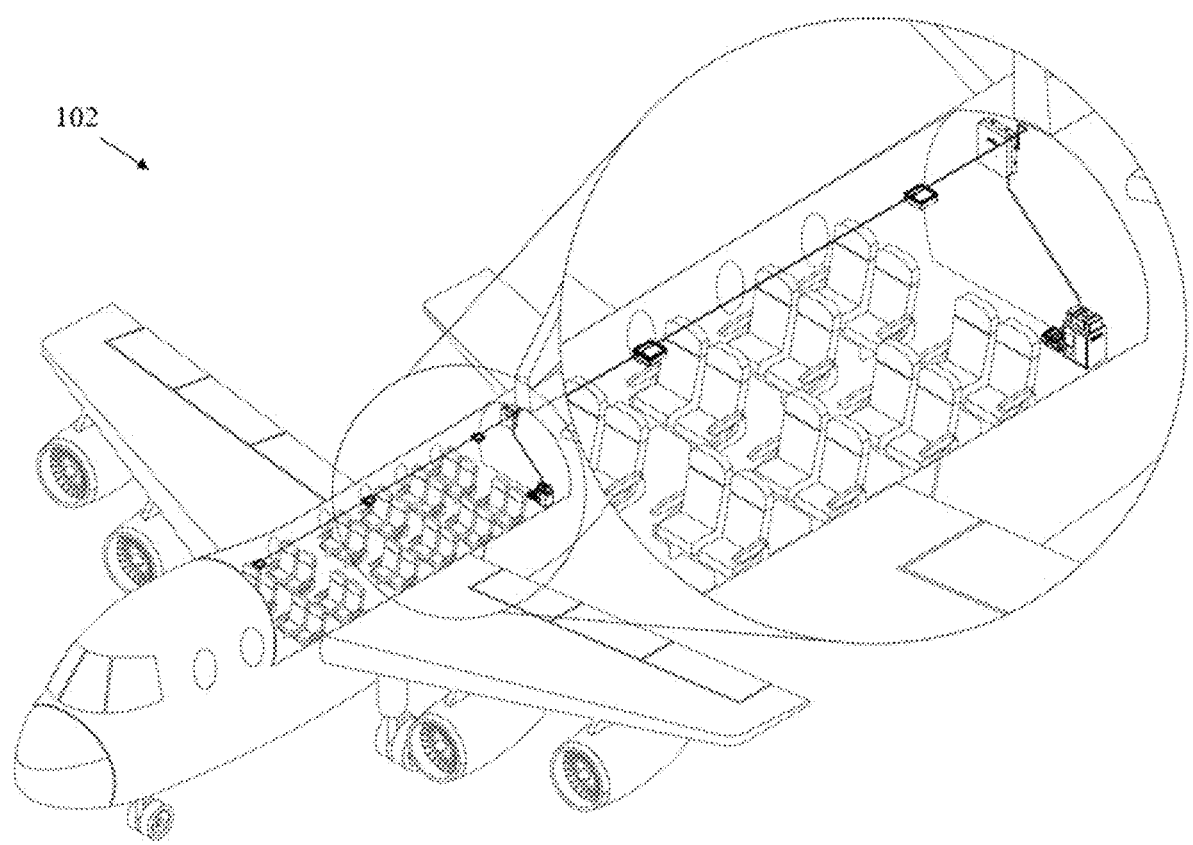
FIG. 13 is a fragmentary, perspective close-up view of an enclosed airplane structure, in accordance with one embodiment of the present invention.
Figure 14:
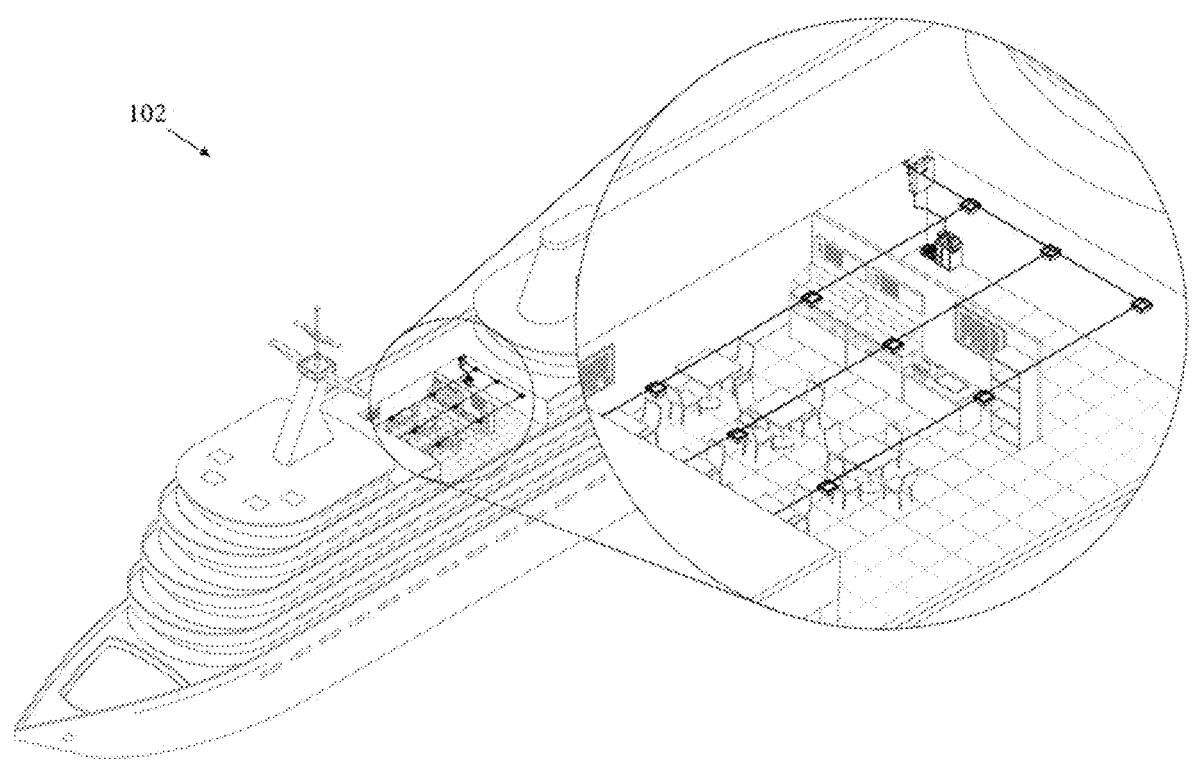
FIG. 14 is a fragmentary, perspective close-up view of an enclosed ship structure, in accordance with one embodiment of the present invention.
Figure 15:
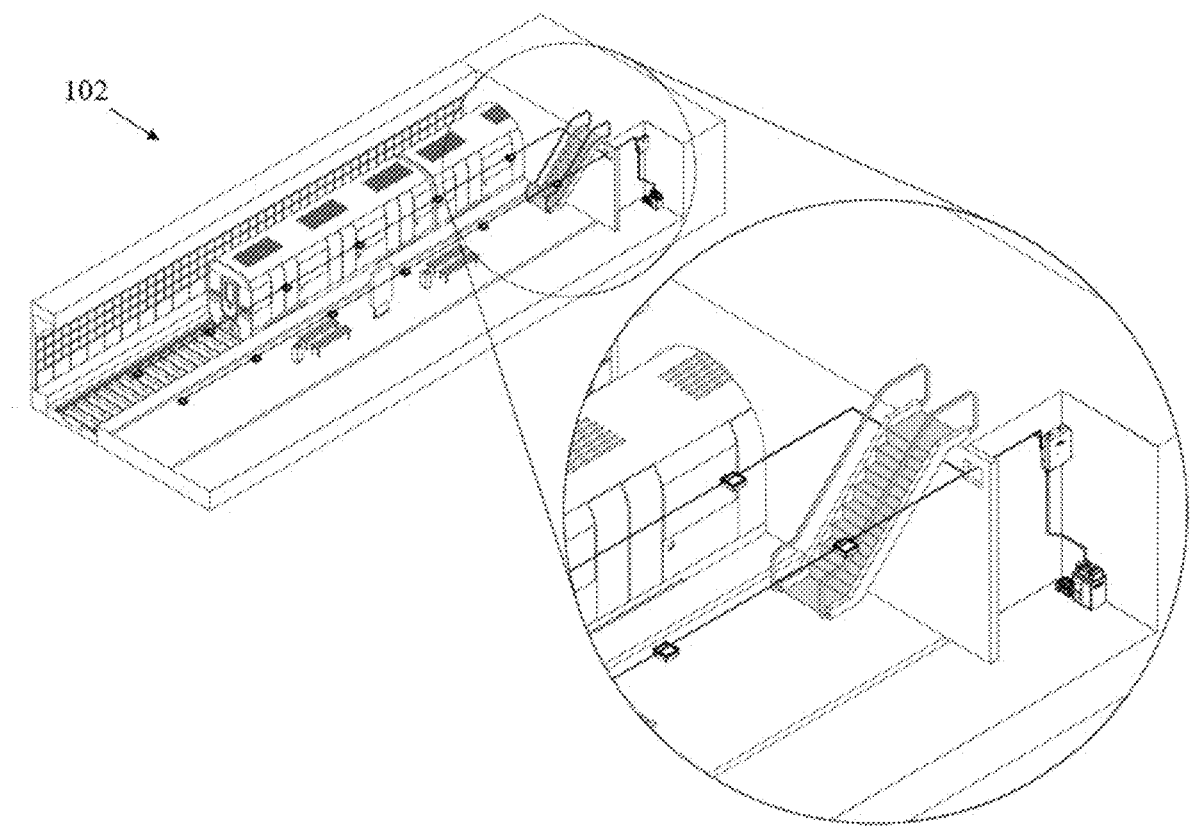
FIG. 15 is a fragmentary, perspective close-up view of an enclosed subway structure, in accordance with one embodiment of the present invention.

The electronically controlled tank valve 1102 is best depicted in the schematic diagram of FIG. 11. As depicted in FIG. 11, the electronically controlled tank valve 1102 is fluidly coupled to the liquid conduit assembly 116 and is disposed upstream of the filtering unit 1008. The electronically controlled tank valve 1102 is operably configured to selectively modulate the flow of liquid from the liquid supply source 1100, particularly in the event of an emergency or foreign infiltration of the liquid supply source 1100 or for purposes of conducting maintenance or repairs on any of the components of the system 100 that are disposed downstream of the electronically controlled tank valve 1102.

Figure 10:
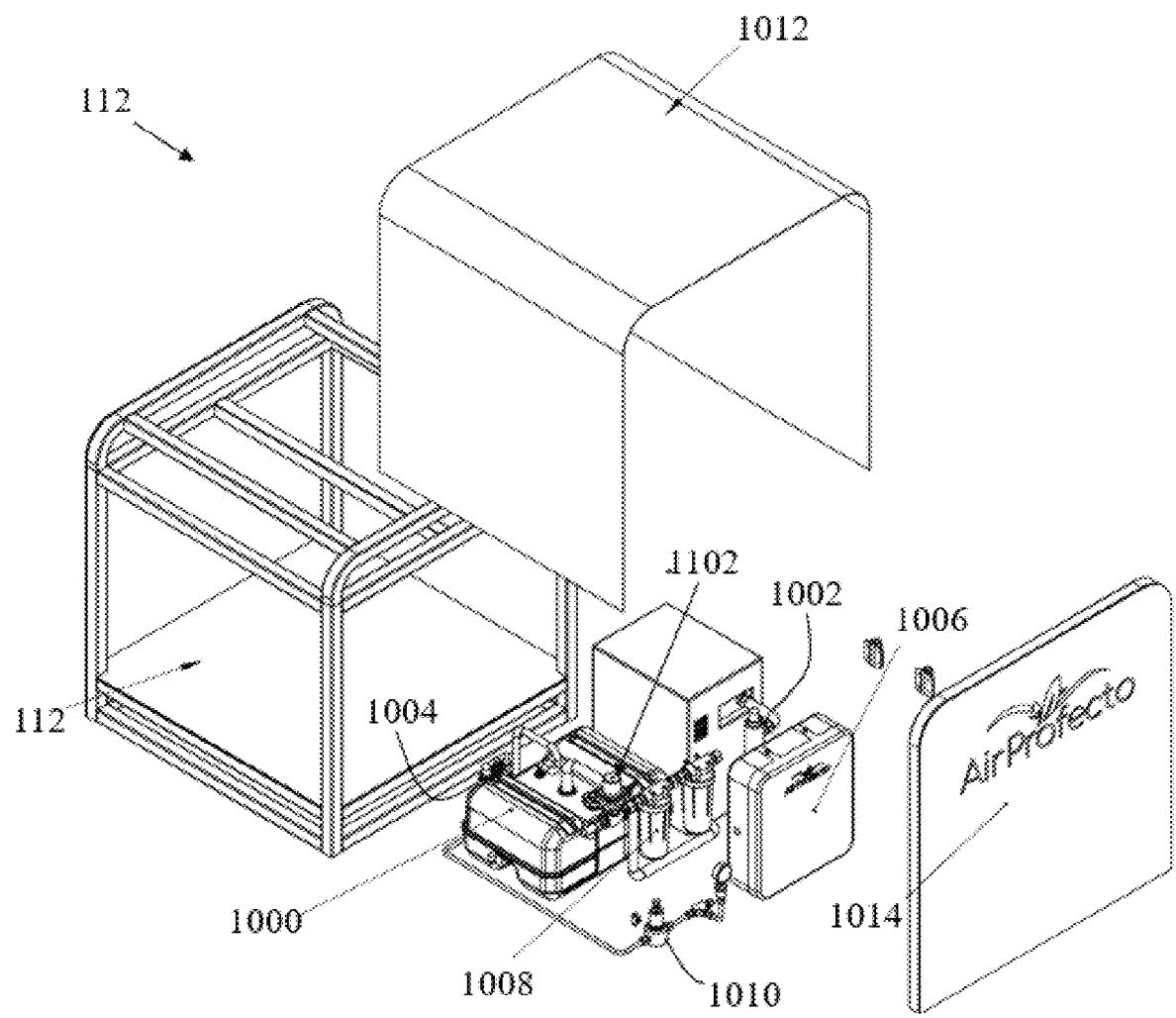
FIG. 10 is an exploded, perspective top view of a liquid supply housing, in accordance with the present invention.

As depicted in FIG. 10, the system 100 further comprises a disinfectant supply pump 1004 housed within the liquid supply housing 112 and operably configured to receive the disinfectant solution 114 and induce, within the liquid conduit assembly 116, a selectively controlled flow rate thereon downstream of the liquid disinfectant storage tank 1000 and to an electronically controlled room pressure regulation component 800 fluidly coupled to the liquid conduit assembly 116 and housed within at least one intermediate regulation housing 118 coupled to the structure sidewall 104. In embodiments where the system 100 is utilized in a building with multiple rooms or floors, each room or floor may have its own intermediate regulation housing 118 coupled to the structure sidewall 104 thereof, with the electronically controlled room pressure regulation component 800 within the intermediate regulation housing 118 selectively regulating and controlling the pressure with which the disinfectant solution 114 is being emitted into the room or floor within which it is located. Each of the pressure regulation components utilized in the system may also include, in lieu or in addition to the pressure regulation components, a sensor operably configured to detect pressure and/or flow within a conduit.

In accordance with a further feature of the present invention, the system 100 comprises an electronically controlled pump pressure regulation component 1010 housed within the liquid supply housing 112 and fluidly coupled to the liquid conduit assembly 116 downstream of the disinfectant supply pump 1004 and upstream of the electronically controlled room pressure regulation component 800. The electronically controlled pump pressure regulation component 1010 is operably configured to selectively regulate and control the pressure with which the disinfectant solution 114 is fluidly transported, through the liquid conduit assembly 116, to the at least one intermediate regulation housing 118 coupled to the structure sidewall 104 of the enclosed room space 110. In an exemplary embodiment, the electronically controlled pump pressure regulation component 1010 consists of a valve that may be manually or automatically selectively manipulated through the at least one electronic control unit 1104, though in alternate embodiments the electronically controlled pump pressure regulation component 1010 may also include or be a flow meter and/or differential pressure transducer operably configured to achieve the same function.

The system 100 also comprises at least one disinfectant emission housing 120a-n coupled to the ceiling 108 and including an emission lower wall 502, an emission housing sidewall 500a surrounding and coupled to the emission lower wall 502, and at least one emission nozzle 200 retained thereon, fluidly coupled to the liquid conduit assembly 116, and operably configured to emit an atomized spray of the disinfectant solution 114 through an emission port 508, 602 defined thereon, in a direction away from the at least one disinfectant emission housing 120a-n, and into the enclosed room space 110. The at least one disinfectant emission housing 120a-n may be of a waterproof, flexibly resilient, and/or deformable material, e.g., natural rubber, PVC, etc. In one embodiment, a single emission port 508 is disposed on the emission lower wall 502 to ultrasonically diffuse the disinfectant solution 114 into the enclosed room space 110 and beneficially cover a large surface area of the enclosed room space 110. In another embodiment, at least one emission port 602a-n, wherein "n" refers to any number greater than one, is disposed on each emission housing sidewall 500a-n to ultrasonically diffuse the disinfectant solution 114 into the enclosed room space 110 with a consistent droplet size. The at least one emission nozzle 200 emits the disinfectant solution 114 through the emission port 508, 602 and, in a preferred embodiment, is operably configured in an 80° spray angle so as to cover a greater area and volume of the enclosed room space 110. The dimensions and configuration of the at least one emission nozzle 200 may vary in alternate embodiments but an exemplary emission nozzle 200 has an air pressure of 5.2 bar, a water pressure of 1.5 bar, an air consumption of 115 liters per hour, a water consumption of 7.1 liters per hour, and a droplet size of 5-10 microns. An excessively high droplet size may result in the accrual of liquid droplets on people and tangible items located within the enclosed room space 110, which may cause damage to tangible items and belongings or discomfort or an inconvenience to individuals.

The number of emission nozzles 200 optimally required for any given enclosed room space 110 depends on the height and the floor area of the enclosed structure 102. To calculate the number of nozzles/humidifiers required, the following formula or equation may be used:

$$\text{Number of nozzles required} = \frac{\text{Area of the room}}{\text{The area covered by a nozzle}}$$

In an alternate embodiment of the present invention, the plurality of disinfectant emission housings 120a-n are each coupled to the ceiling 108 in a distribution configuration operably configured to supply the atomized spray of the disinfectant solution 114 to at least 90% of a room area of the enclosed room space 110.

As depicted in FIG. 1, the distribution configuration may consist of a circular or ring-like configuration wherein the plurality of disinfectant emission housings 120a-n are configured into a ring to minimize any resulting pressure drop of the disinfectant solution 114.

In accordance with a further feature, the system 100 also comprises at least one electronic control unit 1104 communicatively coupled to the electronically controlled tank valve 1102, the disinfectant supply pump 1004, the electronically controlled room pressure regulation component 800, and the electronically controlled pump pressure regulation component 1010 and operably configured to selectively regulate pressure within the liquid conduit assembly 116 and selectively induce the controlled flow rate through the disinfectant supply pump 1004 and cause emission of the atomized spray of the disinfectant solution 114 through the emission port on the at least one disinfectant emission housing 120a-n and into the enclosed room space 110 and at selectively controlled time intervals through use of a programmable timer. The at least one electronic control unit 1104 may include one or more network interface cards (NIC) or a network controller. In some embodiments, the at least one electronic control unit 1104 may include a personal area network (PAN) interface. The PAN interface may provide the capability to selectively regulate pressure within the liquid conduit assembly 116 and selectively induce the controlled flow rate through the disinfectant supply pump 1004 and cause emission of the atomized spray of the disinfectant solution 114 using a short-range communication protocol, for example, a Bluetooth communication protocol. The PAN interface may permit the at least one disinfectant emission housing 120a-n and/or the liquid supply housing 112 to connect wirelessly to one another or to the at least one electronic control unit 1104 via a peer-to-peer connection. The at least one electronic control unit 1104 may also include a local area network (LAN) interface. The LAN interface may be, for example, an interface to a wireless LAN, such as a Wi-Fi network. The range of the LAN interface may generally exceed the range available via the PAN interface. Typically, a connection between two electronic devices via the LAN interface may involve communication through a network router or other intermediary device. Additionally, the at least one electronic control unit 1104 may include the capability to connect to a wide area network (WAN) via a WAN interface. The WAN interface may permit a connection to, for example, a cellular mobile communications network. The WAN interface may include communications circuitry, such as an antenna coupled to a radio circuit having a transceiver for transmitting and receiving radio signals via the antenna. The radio circuit may be configured to operate in a mobile communications network, including but not limited to global systems for mobile communications (GSM), code division multiple access (CDMA), wideband CDMA (WCDMA), and the like. The electronic control unit 1104 may be operably configured to initiate a signal to the disinfectant supply pump 1004 to induce a flow of the disinfectant solution 114 through the liquid conduit assembly 116 at selectively controlled rates and times through use of a programmable timer. Said another way, a user may select and/or program the electronic control unit 1104 to control the flow of disinfectant solution 114 through the nozzles 200 and onto desired proximal and ambient surfaces (e.g., up to approximately 10-20 feet) for a desired period of time and/or at select times, thereby reducing the spread or proliferation of bacterial and/or viral infections and diseases.

Figure 9:
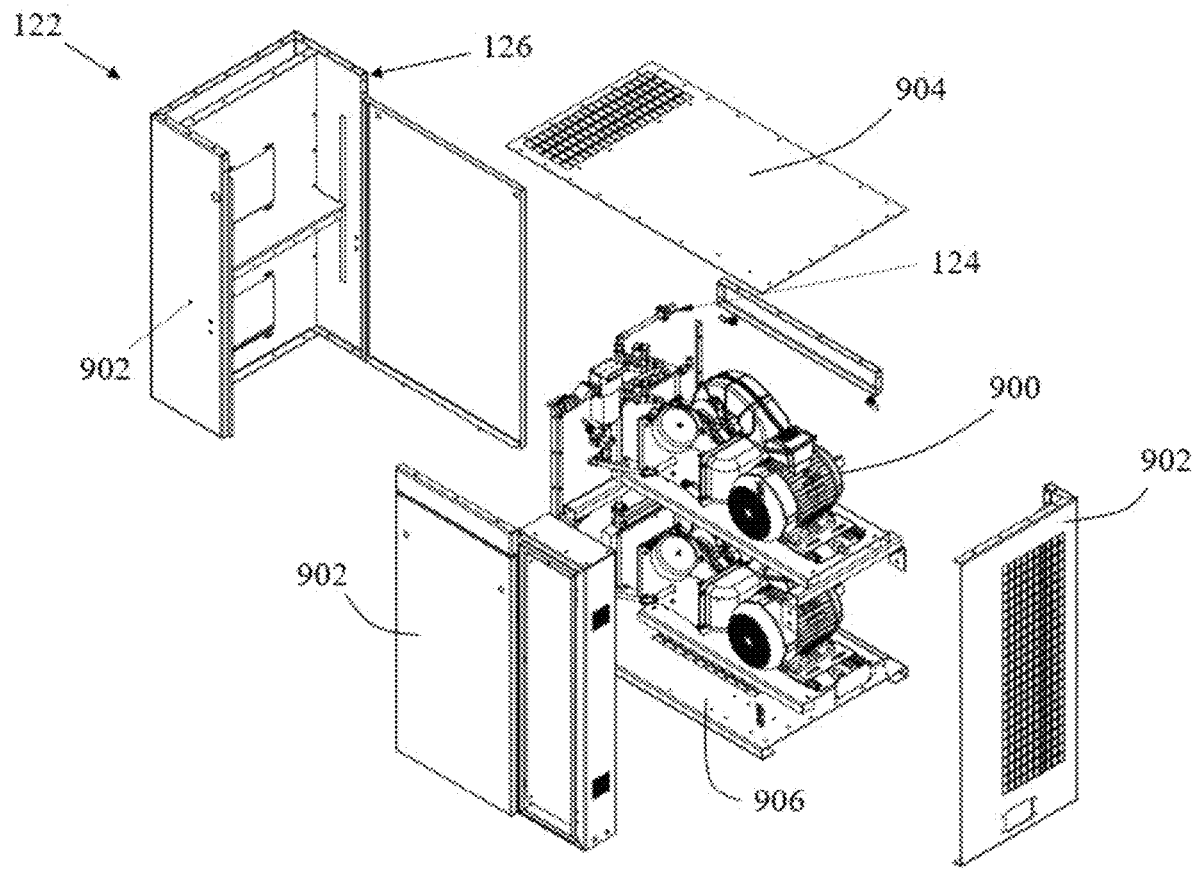
FIG. 9 is an exploded, perspective top view of a compressed air assembly, in accordance with the present invention.

As best depicted in FIG. 4 (C) and FIG. 9, the system 100 may further comprise a compressed air assembly 122 having a compressor 900 operably configured to compress a gas downstream of the compressor 900 within a gas conduit assembly 124 spanning from the compressor 900 to the at least one emission nozzle 200 on the least one disinfectant emission housing 120a-n. The compressed air assembly 122 serves the beneficial function of aerating or atomizing the disinfectant solution 114 such that, when the disinfectant solution 114 is emitted and disseminated throughout the enclosed structure 102, it is in a gaseous, as opposed to liquid, form which then aids to disseminate the disinfectant solution 114 throughout a greater volume and surface area of the enclosed room space 110. The compressed air assembly 122 may be housed in its own independent gas supply housing 126 or may be housed within the liquid supply housing 112. As seen in FIG. 9, the independent gas supply housing 126 of the compressed air assembly 122 comprises a sidewall 902, an upper wall 904, and a lower wall 906. Exemplary dimensions of the compressor 900 are 135 cm by 115 cm by 145 cm. In a preferred embodiment, the compressor 900 is of a screw type, with a weight ranging approximately between 960 kg and 1000 kg, a working pressure ranging approximately between 6 bar and 10 bar, a flow rate of approximately 6.5 cubic meters per minute, and IP 55 protection. The foregoing dimensions and configurations of the compressor 900 may vary in alternate embodiments.

Figure 8:
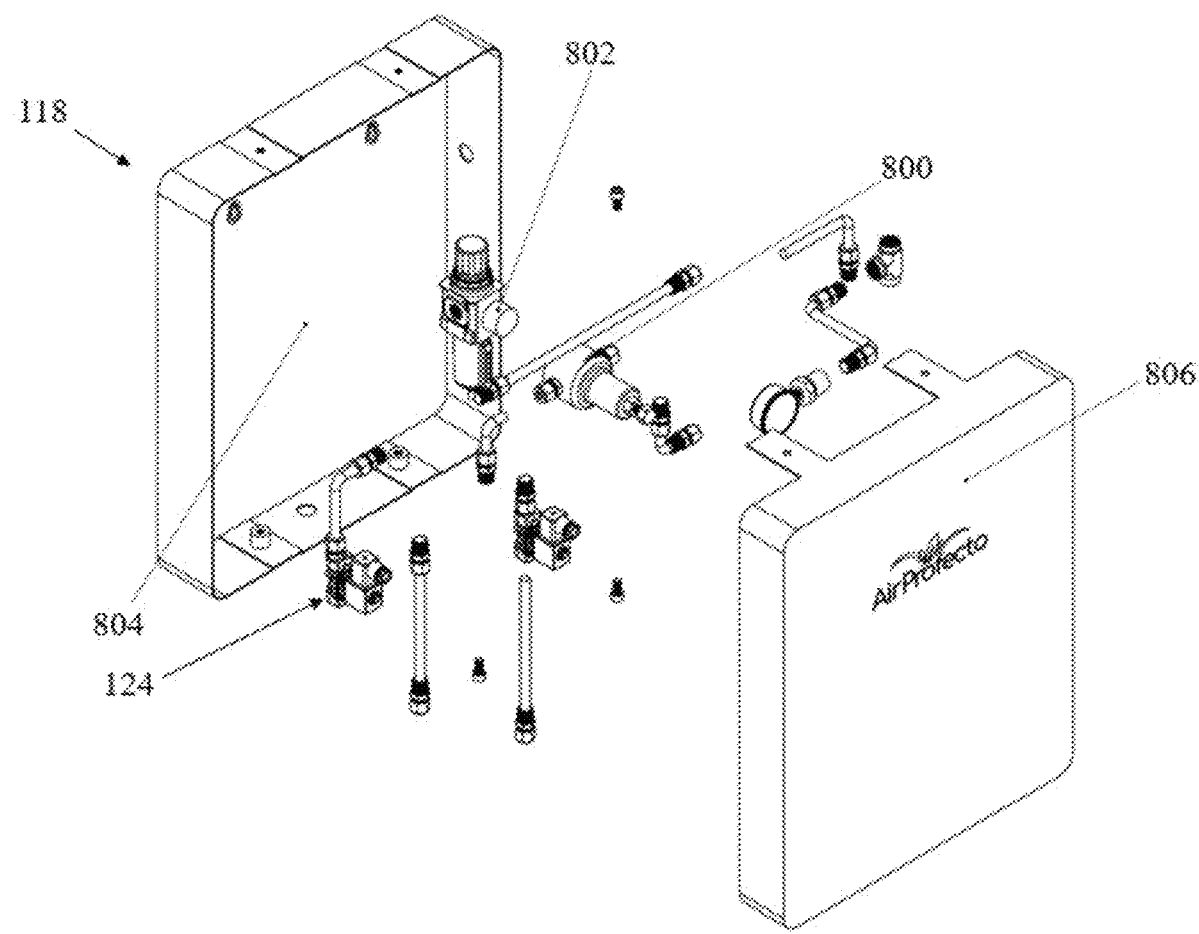
FIG. 8 is an exploded, perspective side view of an intermediate regulation housing, in accordance with the present invention.

In accordance with yet another feature of the present invention, the system 100 also comprises an electronically controlled room air pressure regulator 802 (as seen in FIG. 8) housed within the at least one intermediate regulation housing 118, fluidly coupled to the gas conduit assembly 124 upstream of the at least one emission nozzle 200 and downstream of the compressor 900, and operably configured to selectively modulate, through the at least one electronic control unit 1104 communicatively coupled thereto, the gas pressure within the gas conduit assembly 124 downstream to the at least one emission nozzle 200, thereby causing an increased velocity distribution of the atomized spray of the disinfectant solution 114 through the emission port 508 on the at least one disinfectant emission housing 120. In one embodiment, each of the intermediate regulation housings 118 may include, as best seen in FIG. 8, a rear panel 804 and a front panel 806 selectively removably couplable together with, for example, one or more fastener(s).

As best depicted in the schematic diagram of FIG. 11 and the exploded perspective view of FIG. 9, the gas supply housing 126 with the compressor 900 housed therein, may further comprise a refrigerated air dryer unit 1106 fluidly coupled to the gas conduit assembly 124 downstream of the compressor 900, and at least one filtering unit 1108 fluidly coupled to the gas conduit assembly 124 downstream of the compressor 900 and the refrigerated air dryer unit 1106. The at least one filtering unit 1108 filters the gas within the gas conduit assembly 124 such that the atomized spray of the disinfectant solution 114 that is ultimately emitted consists of sanitized, disinfected, and filtered particles.

The system 100 may further comprise an electronically controlled emission pressure regulation component 202 (best seen in FIG. 2(A)) housed within the at least one disinfectant emission housing 120*a-n*, fluidly coupled to the liquid conduit assembly 116 downstream of the electronically controlled room pressure regulation component 800, and communicatively coupled to the at least one electronic control unit 1104. The electronically controlled emission pressure regulation component 202 consists of a valve that may be manually or automatically selectively manipulated through the at least one electronic control unit 1104, though in alternate embodiments the electronically controlled emission pressure regulation component 202 may also include or be a flow meter and/or differential pressure transducer operably configured to achieve the same function, i.e., to selectively modulate or regulate the pressure with which the atomized spray of the disinfectant solution 114 is released and emitted into the enclosed room space 110.

In a preferred embodiment, the liquid supply housing 112 further comprises a distribution unit 1006 housed therein and with a plurality of liquid conduits forming part of the liquid conduit assembly 116 and operably configured to retain disinfectant solution 114 downstream of the disinfectant supply pump 1004, the plurality of liquid conduits spanning to separate and respective electronically controlled room pressure regulation components 800 fluidly coupled thereto and housed within respective intermediate regulation housings 118 coupled to respective structure sidewalls 104 in respective enclosed room spaces 110. The distribution unit 1006 is schematically disclosed in FIG. 11 and is depicted in FIG. 10.

In accordance with a further feature of one embodiment of the present invention, the at least one disinfectant emission housing 120 further comprises the at least one emission port 602*a-n* defining on four opposing sides of the housing sidewall 500 of the at least one disinfectant emission housing 120; and a fan 700 and an ultrasonic humidifier 702 housed therein and operably configured to emit the atomized spray of the disinfectant solution 114 through the emission ports 602*a-n* defined on the four opposing sides of the housing sidewall 500 of the at least one disinfectant emission housing 120. The at least one disinfectant emission housing 120 may also comprise an upper wall 704 operably configured to selectively attach or affix to the ceiling wall 108 of the enclosed structure 102 and a disinfectant solution inlet valve 706 designed to receive, through the liquid conduit assembly 116, the disinfectant solution 114. The fan 700 is operably configured, based on manual or automatic control from the at least one electronic control unit 1104, to further disseminate the atomized spray of the disinfectant solution 114 generated from the nozzles 200.

What is claimed is:

1. A disinfectant misting system implemented within an enclosed structure having a structure sidewall, a ground wall, and a ceiling wall defining an enclosed room space and comprising:

a liquid supply housing with a liquid disinfectant storage tank housing a disinfectant solution and fluidly couplable, through a liquid conduit assembly, with a disinfectant generation unit fluidly couplable, through the liquid conduit assembly, to a liquid supply source, the liquid disinfectant storage tank and the disinfectant generation unit selectively fluidly couplable, through the liquid conduit assembly, to one another through an electronically controlled tank valve;

a disinfectant supply pump housed within the liquid supply housing and operably configured to receive the disinfectant solution and induce, within the liquid conduit assembly, a selectively controlled flow rate thereon downstream of the liquid disinfectant storage tank and to an electronically controlled room pressure regulation component fluidly coupled to the liquid conduit assembly and housed within at least one intermediate regulation housing coupled to the structure sidewall;

an electronically controlled pump pressure regulation component housed within the liquid supply housing and fluidly coupled to the liquid conduit assembly downstream of the disinfectant supply pump and upstream of the electronically controlled room pressure regulation component;

at least one disinfectant emission housing coupled to a ceiling and including an emission lower wall, an emission housing sidewall surrounding and coupled to the emission lower wall, and at least one emission nozzle retained thereon, fluidly coupled to the liquid conduit assembly, and operably configured to emit an atomized spray of the disinfectant solution through an emission port defined thereon, in a direction away from the at least one disinfectant emission housing, and into the enclosed room space; and at least one electronic control unit communicatively coupled to the electronically controlled tank valve, the disinfectant supply pump, the electronically controlled room pressure regulation component, and the electronically controlled pump pressure regulation component and operably configured to selectively regulate pressure within the liquid conduit assembly and selectively induce the controlled flow rate through the disinfectant supply pump and cause emission of the atomized spray of the disinfectant solution through the emission port on the at least one disinfectant emission housing and into the enclosed room space and at selectively controlled time intervals through use of a programmable timer.

2. The disinfectant misting system according to claim 1, further comprising:

a compressed air assembly having a compressor operably configured to compress a gas downstream of the compressor within a gas conduit assembly spanning from the compressor to the at least one emission nozzle on the least one disinfectant emission housing; and an electronically controlled room air pressure regulator housed within the at least one intermediate regulation housing, fluidly coupled to the gas conduit assembly upstream of the at least one emission nozzle and downstream of the compressor, and operably configured to selectively modulate, through the at least one electronic control unit communicatively coupled thereto, the gas pressure within the gas conduit assembly downstream to the at least one emission nozzle, thereby causing an increased velocity distribution of the atomized spray of the disinfectant solution through the emission port on the at least one disinfectant emission housing.

3. The disinfectant misting system according to claim 2, further comprising:

a gas supply housing with the compressor housed therein, with a refrigerated air dryer unit fluidly coupled to the gas conduit assembly downstream of the compressor, and with at least one filtering unit fluidly coupled to the gas conduit assembly downstream of the compressor and the refrigerated air dryer unit.

4. The disinfectant misting system according to claim 1, further comprising:

a plurality of disinfectant emission housings each including the emission lower wall, the emission housing sidewall surrounding and coupled to the emission lower wall, with the at least one emission nozzle retained thereon, and coupled to the ceiling in a distribution configuration operably configured to supply the atomized spray of the disinfectant solution to at least 90% of a room area of the enclosed room space.

5. The disinfectant misting system according to claim 1, wherein:

the disinfectant generation unit is operably configured to generate the disinfectant solution by subjecting a liquid substance from the liquid supply source to an electrolytic chemical reaction within the disinfectant generation unit.

6. The disinfectant misting system according to claim 5, further comprising:

a filtering unit fluidly coupled to the liquid conduit assembly and disposed downstream of the liquid supply source and upstream of the disinfectant generation unit.

7. The disinfectant misting system according to claim 5, wherein:

the disinfectant solution is hypochlorous acid.

8. The disinfectant misting system according to claim 1, further comprising:

an electronically controlled emission pressure regulation component housed within the at least one disinfectant emission housing, fluidly coupled to the liquid conduit assembly downstream of the electronically controlled room pressure regulation component, and communicatively coupled to the at least one electronic control unit.

9. The disinfectant misting system according to claim 1, wherein the liquid supply housing further comprises:

a distribution unit housed therein and with a plurality of liquid conduits forming part of the liquid conduit assembly and operably configured to retain disinfectant solution downstream of the disinfectant supply pump, the plurality of liquid conduits spanning to separate and respective electronically controlled room pressure regulation components fluidly coupled thereto and housed within respective intermediate regulation housings coupled to respective structure sidewalls in respective enclosed room spaces.

10. The disinfectant misting system according to claim 1, wherein the at least one disinfectant emission housing further comprises:

an emission port defined on each of four opposing sides of the housing sidewall of the at least one disinfectant emission housing; and a fan and an ultrasonic humidifier housed therein and operably configured to emit the atomized spray of the disinfectant solution through the emission ports defined on the four opposing sides of the housing sidewall of the at least one disinfectant emission housing.

11. A disinfectant misting system implemented within an enclosed structure having a structure sidewall, a ground wall, and a ceiling wall defining an enclosed room space and comprising:

a liquid supply housing with a liquid disinfectant storage tank housing a disinfectant solution and fluidly couplable, through a liquid conduit assembly, with a disinfectant generation unit fluidly couplable, through the liquid conduit assembly, to a liquid supply source, the liquid disinfectant storage tank and the disinfectant generation unit selectively fluidly couplable, through the liquid conduit assembly, to one another through an electronically controlled tank valve;

a disinfectant supply pump housed within the liquid supply housing and operably configured to receive the disinfectant solution and induce, within the liquid conduit assembly, a selectively controlled flow rate thereon downstream of the liquid disinfectant storage tank and to an electronically controlled room pressure regulation component fluidly coupled to the liquid conduit assembly and housed within at least one intermediate regulation housing coupled to the structure sidewall;

at least one disinfectant emission housing coupled to the ceiling and including an emission lower wall, an emission housing sidewall surrounding and coupled to the emission lower wall, and at least one emission nozzle retained thereon, fluidly coupled to the liquid conduit assembly, and operably configured to emit an atomized spray of the disinfectant solution through an emission port defined thereon, in a direction away from the at least one disinfectant emission housing, and into the enclosed room space;

a compressed air assembly having a compressor operably configured to compress a gas downstream of the compressor within a gas conduit assembly spanning from the compressor to the at least one emission nozzle on the least one disinfectant emission housing; and at least one electronic control unit communicatively coupled to a electronically controlled tank valve, the compressor, the disinfectant supply pump, the electronically controlled room pressure regulation component, and the electronically controlled pump pressure regulation component and operably configured to selectively regulate pressure within the liquid conduit assembly and selectively induce the controlled flow rate through the disinfectant supply pump and cause emission of the atomized spray of the disinfectant solution through the emission port on the at least one disinfectant emission housing and into the enclosed room space and at selectively controlled time intervals through use of a programmable timer.

12. The disinfectant misting system according to claim 11, wherein:

the electronically controlled pump pressure regulation component housed within the liquid supply housing and fluidly coupled to the liquid conduit assembly downstream of the disinfectant supply pump and upstream of the electronically controlled room pressure regulation component.

13. The disinfectant misting system according to claim 12, further comprising:

an electronically controlled room air pressure regulator housed within the at least one intermediate regulation housing, fluidly coupled to the gas conduit assembly upstream of the at least one emission nozzle and downstream of the compressor, and operably configured to selectively modulate, through the at least one electronic control unit communicatively coupled thereto, the gas pressure within the gas conduit assembly downstream to the at least one emission nozzle, thereby causing an increased velocity distribution of the atomized spray of the disinfectant solution through the emission port on the at least one disinfectant emission housing.

14. The disinfectant misting system according to claim 13, further comprising:

a gas supply housing with the compressor housed therein, with a refrigerated air dryer unit fluidly coupled to the gas conduit assembly downstream of the compressor, and with at least one filtering unit fluidly coupled to the gas conduit assembly downstream of the compressor and the refrigerated air dryer unit.

15. The disinfectant misting system according to claim 14, further comprising:

a plurality of disinfectant emission housings each including the emission lower wall, the emission housing sidewall surrounding and coupled to the emission lower wall, with the at least one emission nozzle retained thereon, and coupled to the ceiling in a distribution configuration operably configured to supply the atomized spray of the disinfectant solution to at least 90% of a room area of the enclosed room space.

16. The disinfectant misting system according to claim 11, wherein:

the disinfectant generation unit is operably configured to generate the disinfectant solution by subjecting a liquid substance from the liquid supply source to an electrolytic chemical reaction within the disinfectant generation unit.

17. The disinfectant misting system according to claim 16, further comprising:

a filtering unit fluidly coupled to the liquid conduit assembly and disposed downstream of the liquid supply source and upstream of the disinfectant generation unit.

\* \* \* \* \*